United States Patent [19]

Planck et al.

[11] Patent Number: 5,104,398
[45] Date of Patent: Apr. 14, 1992

[54] PROCESS FOR THE TREATMENT OF A SURGICAL SUTURING THREAD AND SURGICAL SUTURING THREAD

[75] Inventors: Heinrich Planck, Nuertingen; Erhard Mueller, Stuttgart, both of Fed. Rep. of Germany

[73] Assignee: Deutsche Institute für Textil-und Faserforschung Stuttgart - Stiftung des öffentlichen Rechts, Fed. Rep. of Germany

[21] Appl. No.: 648,545

[22] Filed: Jan. 30, 1991

[30] Foreign Application Priority Data

Jan. 30, 1990 [DE] Fed. Rep. of Germany ....... 4002626

[51] Int. Cl.⁵ .................. A61B 17/00; A01N 1/02
[52] U.S. Cl. .................. 606/230; 606/231; 427/2
[58] Field of Search .......... 472/2; 428/263, 378; 606/230, 231

[56] References Cited

U.S. PATENT DOCUMENTS

| | | |
|---|---|---|
| 4,185,637 | 1/1980 | Mattei .................. 606/230 |
| 4,201,216 | 5/1980 | Mattei .................. 606/230 |
| 4,532,929 | 8/1985 | Mattei .................. 606/230 |
| 4,624,256 | 11/1986 | Messier et al. .......... 606/230 |
| 4,705,820 | 11/1987 | Wang et al. ............ 606/230 |
| 4,711,241 | 12/1987 | Lehmann ............... 606/231 |
| 4,713,075 | 12/1987 | Kurland ................ 606/230 |
| 5,037,950 | 8/1991 | Bezwada et al. ......... 606/230 |

FOREIGN PATENT DOCUMENTS 2638831 10/1977 Fed. Rep. of Germany.
2755344 6/1978 Fed. Rep. of Germany.
2921810 12/1979 Fed. Rep. of Germany.

Primary Examiner—Stephen C. Pellegrino
Assistant Examiner—Gary Jackson
Attorney, Agent, or Firm—Eckert Seamans Cherin & Mellott

[57] ABSTRACT

A surgical suturing thread is coated with a fatty acid metal salt. For this purpose it is dissolved in an organic solvent and the suturing thread is coated with the hot solution, whose temperature is so high that the fatty acid metal salt remains in the dissolved state. The solvent is then evaporated from the thus applied coating at elevated temperature.

12 Claims, 2 Drawing Sheets

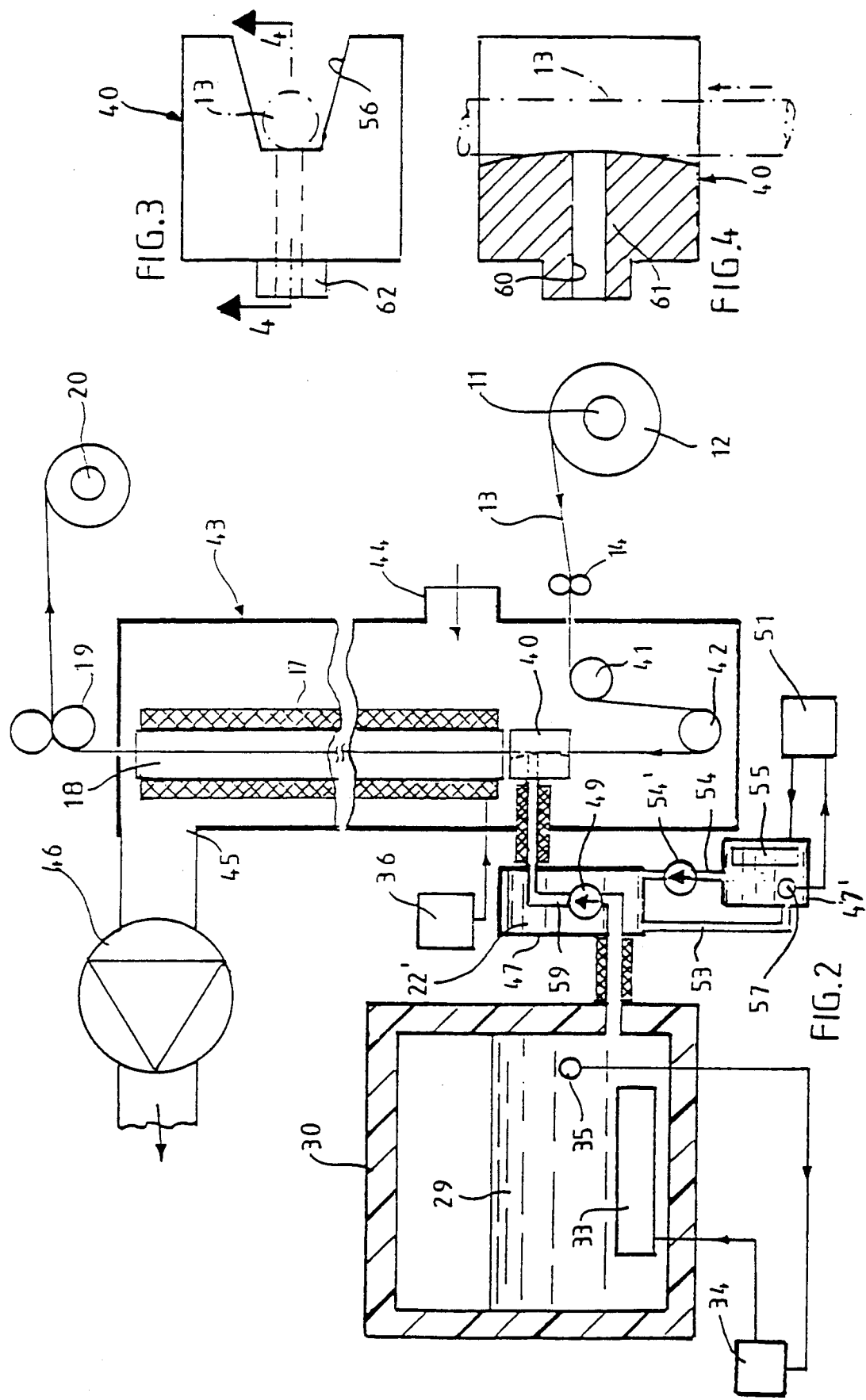

PROCESS FOR THE TREATMENT OF A SURGICAL SUTURING THREAD AND SURGICAL SUTURING THREAD

BACKGROUND OF THE INVENTION

The invention relates to a process for the treatment of a surgical suturing, stitching or sewing thread according to the preamble of claim 1 and to a surgical suturing, sewing or stitching thread produced by this process.

A multithread suture material is known, which for improving the knotting characteristics is coated with approximately 1 to 5% by weight of the dry residue of a substance containing a gel of a fatty acid salt with 6 or more carbon atoms with a polyvalent metal ion in a volatile organic solvent (DE-OS 29 21 810). This multithread suture material is a surgical suturing thread. The preparation of the gel used for coating purposes is, however, time-consuming and expensive. In addition, on coating with the gel substance, at the point where the suturing thread passes out of the said substance it must be drawn through a soft felt pad, in order to strip off excess coating material and obtain an optimum uniform application. However, this felt pad can be relatively rapidly modified and does not guarantee a uniform coating.

The problem of the present invention is therefore to provide a process of the type defined in the preamble of claim 1 for the treatment of a surgical suturing thread, which also improves the knotting characteristics of said thread, but which can be performed in a time-saving and relatively inexpensive manner and which leads to a good uniformity of the coating.

SUMMARY OF THE INVENTION

According to the invention this problem is solved by the process of claim 1.

In the inventive process the surgical suturing thread is coated by means of a solution containing the fatty acid metal salt dissolved in a solvent. The temperature of the solution during coating is kept sufficiently high to ensure that the fatty acid metal salt remains dissolved. Following the coating of the surgical suturing thread by means of the solution, the solvent is evaporated from the coating for the drying thereof at such a high temperature that, after evaporation, the coating medium remains as a dry residue on the suturing thread.

This inventive process leads to suturing threads with excellent knotting characteristics and, due to the more uniform distribution of the fatty acid metal salt, this can be achieved with a smaller percentage of fatty acid metal salt relative to the total weight of the coated suturing thread, than in the case of the known suturing thread coating with a gel of the same fatty acid metal salt.

The inventive process can also be performed in a time-saving and highly inexpensive manner and leads to a very uniform coating. It is sufficient for the purpose of coating the suturing thread to e.g. merely draw it through the hot solution, which can take place at relatively high feed speeds. Subsequently it is merely necessary to dry the suturing thread, i.e. its coating, at adequately high temperatures, which can e.g. also take place very rapidly in a heated drying chamber or drying tunnel, or merely by blowing hot air or some other hot gas onto it. For this purpose the suturing thread can be continuously passed through the drying chamber or tunnel or the other area immediately following its wetting or impregnating with the solution. Preferably a further drying takes place under reduced pressure, e.g. in a pressure range of a few mbar, in order to remove the final solvent residues.

Thus, the application of the solution to the suturing thread can preferably take place in such a way that the thread is drawn through the solution. It is generally not subsequently necessary, prior to its drying, to partly free the said thread from the solution by a stripping process on a stripper, so that in general after drawing the thread out of the solution it is immediately possible to start drying the adhering solution without any intermediate treatment.

The application of the solution to the surgical suturing thread can also take place in other ways, e.g. by squirting or spraying with the hot solution, or by application by means of one or more applicator rollers, or in some other way.

The fatty acid metal salt can often comprise in a particularly advantageous manner a single chemical compound. However, the fatty acid metal salt can also be constituted by a mixture of salts of several fatty acids.

It is particularly advantageous for the fatty acid metal salt to be a magnesium fatty acid salt, preferably magnesium stearate, and/or a barium salt and/or an aluminium salt and/or a zinc salt and/or a calcium salt, preferably calcium stearate.

The solvent is preferably constituted by a terpene mixture with limonene as the main constituent and as is marketed by Carl Roth GmbH & Co., Karlsruhe under the name Rotihistol. It is also possible to use other suitable solvents e.g. aromatic hydrocarbons, such as benzene, toluene, xylene and mesitylene.

According to a preferred development at least one wax is dissolved or dispersed in the solution, so that on impregnating or wetting the suturing thread with the solution it is deposited on the thread together with the fatty acid metal salt and further improves the knotting characteristics and/or the adhesion of the fatty acid metal salt to the suturing thread, in that it passes as an additional constituent into the coating of the thread. The weight proportion of the wax, based on the total weight of the suturing thread coating, is preferably 10 to 90 and particularly appropriately 20 to 50% by weight. The wax can e.g. be a mixture of nonionic ester, e.g. sorbitan monostearate. It is preferably a nonpolymer wax.

The temperature of the solution on coating the suturing thread must at least be high enough to maintain the fatty acid metal salt in dissolved form in the solvent. The drying of the suturing thread after impregnating or wetting with the solution is also performed at elevated temperatures, in order to obtain good knotting characteristics.

The minimum temperature of the solution on coating the suturing thread, i.e. during its impregnation or wetting with the solution is a function of the fatty acid metal salt and can in many cases, e.g. when the fatty acid metal salt is magnesium stearate, preferably be at least 50° C. and can be higher or lower as a function of said salt.

The suturing thread can be dried in a gaseous atmosphere, preferably air, the minimum temperature of the gas also being dependent on the fatty acid metal salt and the solvent used and can in many cases, e.g. when the salt is constituted by magnesium stearate, preferably be at least 80° C. and is max 200° C.

The invention also extends to a surgical suturing thread provided with a coating according to the invention. Preferably the coating represents approximately 0.5 to 10% by weight of the coated suturing thread.

An embodiment of the invention is described hereinafter relative to the drawings, wherein show:

BRIEF DESCRIPTION OF THE DRAWING

FIGS. 1 and 2 In each case an apparatus for treating surgical suturing threads according to the embodiments of the invention in a substantially diagrammatic, part sectional and broken-away form.

FIG. 3 A plan view of the brightening or reviving pin of the apparatus according to FIG. 2 on a larger scale.

FIG. 4 A section through the brightening or reviving pin according to FIG. 3, considered along the section line 4—4.

Figure 1:
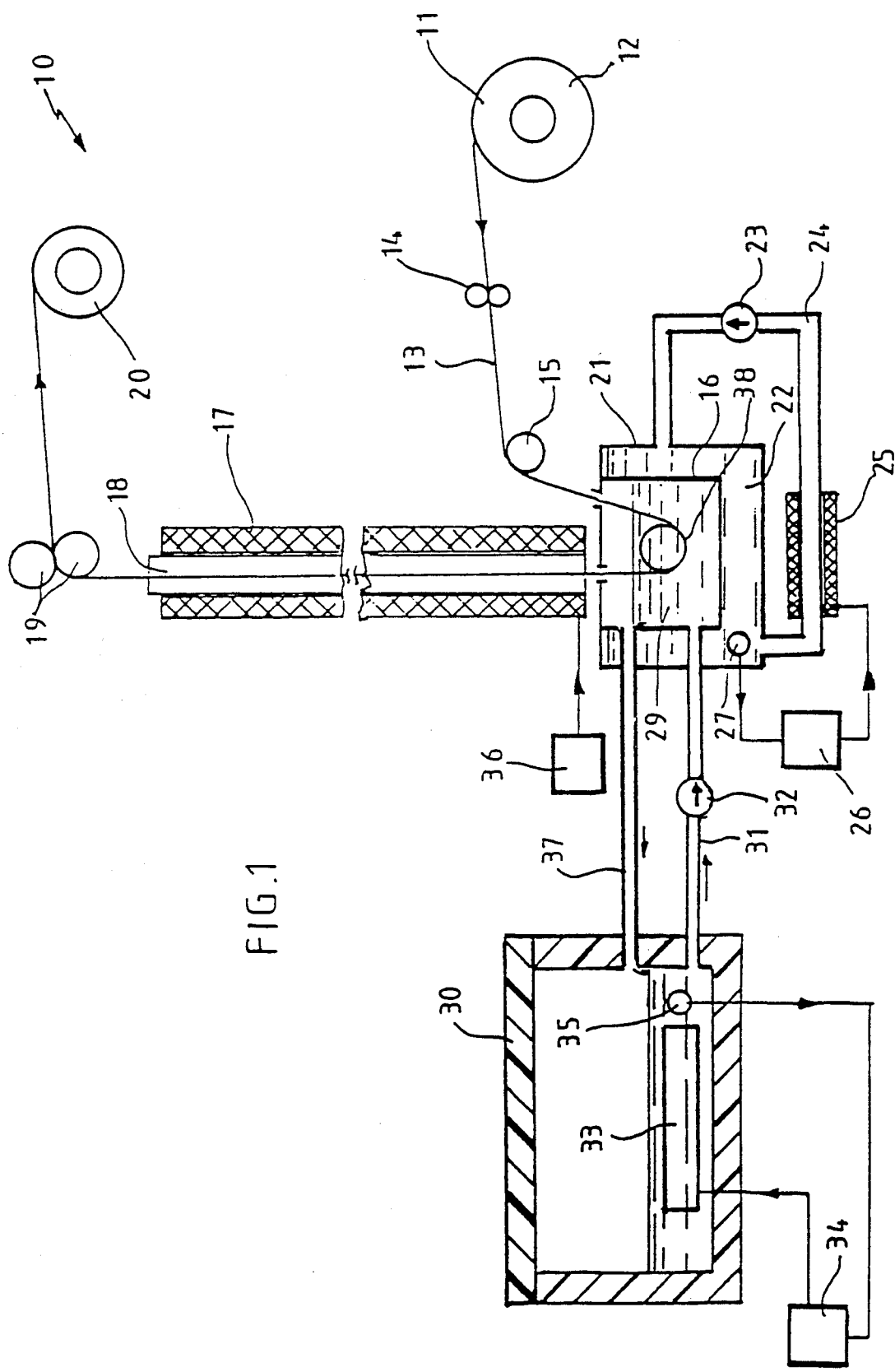

According to FIG. 1 the apparatus 10 has a feed spool 11, whose thread winding body 12 comprises a surgical suturing thread to be coated. The latter is constantly unwound when the apparatus 10 is operating from the said feed reel 12 and then firstly passes through a tensioning thread brake 14 and from the latter to a guide pulley 15. It then passes on to a further guide pulley 38 located in an impregnating tank 16 and then moves vertically upwards through a drying tunnel or channel heated by means of a filament winding 17 to a driven pair of rollers 19 located above said tunnel or channel 18 and which supplies the suturing thread 13 tensioned to a predetermined tension by the thread brake 14 at a constant feed speed of e.g. 3 to 20 m/s to a driven take-up spool 20 onto which it is wound.

The impregnating tank 16 is located within a heating vessel 21, which contains a liquid heating medium 22, e.g. oil having a boiling point above 200° C. and which in the operation of the said apparatus 10 is sucked by means of a pump 23 located in a bypass line 24 leading from the bottom to a side wall of the heating vessel 21 in continuous manner from the latter and is then returned to the same at a point located further upwards. This bypass line 24 has a filament winding 25, which is used for heating the heating medium 22 to a constant temperature by means of a temperature regulator 26 into which is inputted the actual value of the temperature of the heating medium 21 by a temperature sensor 27 located within the heating vessel 21. The temperature regulator 26 compares this actual value with a desired temperature value for the heating medium 22 set on it and controls the energy supplied to the filament winding 25 in such a way that the heating medium temperature measured by the sensor 27 is kept within the heating vessel 21 at roughly the predetermined desired value.

The impregnating tank 16 contains a solution 29 used for impregnating and therefore coating the surgical suturing thread 13. It consists of a solution formed by a solvent and a fatty acid metal salt dissolved therein and having 6 or more carbon atoms. Examples will be given hereinafter. The solution preferably contains a wax comprising fatty acid esters.

The guide pulley 38 positioned in the impregnating tank 16 is immersed in the solution 29 located in the said tank 16 and in this way brings about the immersion of the thread 13 in said solution 29. The solution 29 is not only present in the impregnating tank 16, but also in a storage tank 30 constantly connected thereto via lines 31 and 37.

In operation, the solution 29 located in the storage tank 30 is continuously pumped into the impregnating tank 16 by means of the pump 32 inserted in the connecting line 31 used for connecting the storage tank 30, close to the bottom thereof, with the impregnating tank 16 close to its bottom. Close to the top of the impregnating tank 16, the solution flows back into the storage tank 30 via the roughly horizontal overflow pipe 37.

The solution 29 is heated in the impregnating tank 16 by the heating medium 22 and in the storage tank 30 by an electric heater 33, so that it has within the impregnating tank 16 an adjustable, predetermined high temperature, at which the fatty acid metal salt is reliably completely dissolved in the solvent of the solution 29, i.e. does not gel or disperse.

The heater 33 is connected to a temperature regulator 34, to which a temperature sensor 35 located within the solution 29 in the storage tank 30 and which serves as an actual value sensor. This temperature sensor 35 supplies the actual value of the temperature of the solution 29 in the storage tank 30 to the regulator 34, which compares it with the desired value set thereon and which corresponds to or is slightly higher than the desired temperature value set on the temperature regulator 26 and the regulator 34 controls the heater 33 in such a way that the temperature of the solution 29 in the storage tank 30 constantly approximately corresponds to the desired value of said temperature set on the temperature regulator 34.

Heating current is supplied to the filament winding 17 of the drying tunnel 18 by means of a temperature control device 36 and there can optionally also be a regulation of the temperature of the winding 17. The temperature within the drying tunnel 18 is appropriately approximately the same or higher than the temperature of the solution 29, but can also be somewhat lower as a function of the temperature of the solution 29.

It is important that the temperature of the solution 29 and the air temperature used for drying the suturing thread 13 previously impregnated with the solution 29 in the impregnating tank are set so high that the combination of the fatty acid metal salt and the wax in the solution 29 wetting the thread 13 also remains dissolved during the drying of the thread 13 in the drying tunnel 18, i.e. until evaporation has taken place of the solvent absorbed by the suturing thread 13 in the impregnating tank 16 together with the fatty acid metal salt and wax dissolved therein. Thus, on the suturing thread 13 all that is left behind are the fatty acid metal salt and the wax and as a result its knotting characteristics are considerably improved. Therefore the drying tunnel 18 is heated with such a high temperature that the solvent in said tunnel 18 is completely evaporated from the thread 13 due to the high temperature. Therefore the suturing thread 13 leaves the drying tunnel 18 in the dried state, so that the thread 13 leaves the tunnel 18 only coated with the fatty acid metal salt and the wax as the solid. Thus, the distribution of the fatty acid metal salt and the wax on the surgical suturing thread is particularly uniform and particularly good thread knotting characteristics are obtained. In addition, only very small fatty acid metal salt quantities are required.

In the case of the apparatus 10' according to FIG. 2 the coating of the surgical suturing thread 13 fed at a constant feed rate by means of a driven pair of rollers 19 from a feed spool 11 to a take-up spool 20 takes place by means of a so-called brightening or reviving pin 40, whose construction is shown in greater detail in FIGS. 3 and 4 and which will be explained further hereinafter.

At a limited distance vertically above the brightening pin 40, there is once again a drying tunnel 18 with a filament winding 17, which is supplied with heating current by a temperature control device 36, as in the case of the apparatus 10 according to FIG. 1. A thread brake 14 once again tensions the suturing thread 13 between it and the roller pair 19. Following the thread brake 14, the suturing thread 13 passes via a guide pulley 41 to a lower guide pulley 42 and from the latter vertically upwards to the brightening pin 40. The thread then passes from the latter vertically through the drying tunnel 18 to the pair of drive rollers 19, which forwards it to the driven take-up spool 20.

The brightening pin 40, the guide pulleys 41, 42 and the drying tunnel 18 with the filament winding 17 are located within a heating chamber 43, which is also heated by the winding 17 and which laterally has a single air inlet 44 and on its other side, facing the air inlet 44, and close to its top a single air outlet 45, which is connected to an air feed mechanism, e.g. a fan 46, which maintains the suction of air through the heating chamber 43.

A storage tank 30 contains a solution 29 of wax and fatty acid metal salt dissolved in a solvent, said metal salt containing 6 or more carbon atoms and is kept dissolved in said solution, in that the temperature of the latter is regulated to a high temperature keeping the fatty acid metal salt dissolved by means of a temperature regulator 34. As in the case of the apparatus 10 according to FIG. 1, with the temperature regulator 34 is associated an electric heater 33 controlled by it and located within the solution 29 and also in the latter an actual value temperature sensor 35. The temperature of the solution 29 in the storage tank 30 is kept at a desired value set on the temperature regulator 34, which is high enough to keep the wax and fatty acid metal salt in a dissolved state in the solution 29.

Inside a tank 47 is provided a dosing or metering pump 49 in a line 59 for the hot solution 29 leading from the storage tank 30 to the brightening pin 40, so that said hot solution 29 is fed in a predetermined quantity/time, i.e. in dosed manner to the brightening pin 40. The tank 47 is substantially filled with a liquid heating medium 22', whose temperature is kept by means of a temperature regulator 51 at a level such that its desired value roughly corresponds to the desired value of the temperature of the solution 29 in the storage tank 30. The said tank 47 is connected to a heating container 47' via a forward line 53 and a return line 54. The latter contains a pump 54', which maintains a constant circulation of the liquid heating medium 22' in the containers 47 and 47'. A temperature sensor 57 located in the container 47' and serving as an actual value sensor is connected to the temperature regulator 51, which controls an electric heater 55 located in the container 47' for keeping constant the high temperature of the heating medium 22'. Thus, the dosing pump 49 is kept at the high temperature of the solution 29 flowing through it. The connecting line 59 is well thermally insulated by thermal insulation between the storage tank 30 and the tank 47, as well as between the latter and the brightening pin 40, so that the latter receives the solution 29 delivered by the dosing pump 49 at the high temperature set on the temperature regulator 34 and applies the same to the surgical suturing thread 13 for the coating thereof.

The heater 17 maintains a high temperature in the heating chamber 43 and this also roughly corresponds to the temperature of the solution 29 in the storage tank 30, or can be higher than this, or in some cases even somewhat lower. It is important that the temperature at the brightening pin 40 and also in the following drying tunnel 18, where the solvent of the solution 29 uniformly applied by means of the brightening pin 40 to the suturing thread 13 for the coating thereof is evaporated from said thread 13, is so high that the solvent is removed from the solution 29 and the wax and the fatty acid metal salt remain as a dry residue on the thread 13. The wax and fatty acid metal salt maintain this consistency and correspondingly in this way improve the knotting characteristics of the suturing thread 13.

The feed rate of the suturing thread 13 can appropriately be e.g. 3 to 20 m/s, as a function of the circumstances and can also be higher or lower, as applies in the case of the apparatus according to FIG. 1.

The brightening pin 40 is a solid body made from metal or ceramic, which has a cross-sectionally approximately trapezoidal channel 56, which is open on its wide side and on whose bottom engages the surgical suturing thread 13 indicated in dot-dash line form in FIGS. 3 and 4. According to FIG. 4, the said bottom is convex and is preferably arcuately curved. The vertically moving thread 13 passes over the outlet opening of a channel 60 for the solution 29 penetrating the area 61 and a connecting piece 62 of the brightening pin 40. The solution is fed in a dosed quantity through the dosing pump 49 into the channel 60 and therefore to the thread 13 for the uniform coating thereof. Immediately following the application of the solution to the suturing thread 13, the latter passes from the brightening pin 40 into the drying tunnel 18 and passes through the same without coming into contact with the inner wall thereof and arrives at the driven pair of rollers 19. It is completely dried during its path within the drying tunnel 18, in that in the latter the solvent is evaporated from the solution applied to the thread 13.

The following examples serve to illustrate the invention.

EXAMPLE 1

300 g of calcium stearate and 100 g of wax G1564 (Atlas-Chemie, Essen; mixture of fatty acid esters) are added to 4000 g of Rotihistol (terpene mixture) and is dissolved in 3 hours accompanied by stirring at approximately 130° C. The hot solution is then fed into a storage tank 30 (FIG. 1) heated to 130° C. and is pumped in circuit form through a smaller container 16 also kept at 130° C., cf. FIG. 1. A braided polyethylene terephthalate suturing thread of thickness or strength —3/0— is passed through the hot solution in the container 16 and coated with the said solution. Immediately thereafter the suturing thread is passed through a heating channel or tunnel 17 at 160° C. and the solvent is evaporated. The remaining solvent residue is removed at 50° C. and a vacuum of 1 mbar. Approximately 3% by weight of solid constituents, comprising wax G1564 and calcium stearate, remain on the homogeneously coated thread.

The suturing thread has excellent knotting characteristics in both the dry and wet state. A suturing thread of strength or thickness —0— has comparable characteristics.

EXAMPLE 2

300 g of magnesium stearate and 100 g of wax G1564 were dissolved, accompanied by stirring, in 3 hours at approximately 120° C. in 4000 g of xylene (isomer mixture). The hot solution is fed into a storage tank 30 (FIG. 1) heated to 60° C. and pumped in circuit form through a smaller container 16 also at 60° C. An absorbable, braided, poly-(p-dioxanone) suturing thread of thickness or strength —3/0— is passed through the hot solution in the container 16 and coated with the said solution. Immediately thereafter the suturing thread is passed through a heating tunnel 17 which is at a temperature of 140° C. and the solvent evaporates. The remaining solvent residue is removed at 50° C., whilst storing under a vacuum of 1 mbar. Approximately 3% by weight of solid constituents, comprising the wax G1564 and calcium stearate, remain on the homogeneously coated thread. The suturing thread has excellent knotting characteristics in both the wet and dry states.

EXAMPLE 3

In accordance with the general process of examples 1 and 2 and using benzene, toluene, xylene, mesitylene and Rotihistol as organic solvents with calcium stearate and wax G1564, suture materials are homogeneously coated from the hot solution. In place of the calcium stearate, it is also possible to use magnesium or zinc stearate, which in combination with wax G1564 have similar improved knotting characteristics to the combination of calcium stearate and wax G1564.

EXAMPLE 4

A solution of 100 g of wax G1564, 500 g of calcium stearate and 4000 g of Rotihistol are applied at 120° C. by means of a brightening pin to a poly-(p-dioxanone) suturing thread of thickness or strength —3/0—. The solution is located in a storage tank 30 at 120° C. and by means of a dosing pump 49 at 120° C. is delivered through a heated copper pipe to the brightening pin 40, which is also heated to 120° C., cf. FIGS. 2 to 4. The thread is led past the outlet 60 of the brightening pin 40 and is uniformly coated with the solution. Immediately following this the thread is passed through a heating tunnel 17 at 140° C. and is substantially freed from the solvent. The remaining solvent residue is removed at 50° C., whilst keeping the thread under a vacuum of 1 mbar.

Approximately 5% by weight solid constituents, comprising wax G1564 and calcium stearate, remain on the homogeneously coated suturing thread. The suturing thread has excellent knotting characteristics in both the wet and dry states.

EXAMPLE 5

In accordance with the process of example 4 and using benzene, toluene, xylene, mesitylene and Rotihistol as organic solvents and with wax G1564 and calcium stearate, suture materials are coated from a hot solution by means of a brightening pin. It is possible to replace the calcium stearate by magnesium or zinc stearate, which when combined with wax G1564 have similar improved knotting characteristics to a combination of wax G1564 and calcium stearate. As zinc is very important for healing wounds, the use of zinc stearate can be particularly favourable from the pharmacological standpoint.

Apart from the aforementioned constituents, the coating can also contain constituents necessary for the intended use, such as e.g. antibiotics, antiseptics, antiphlogistics, dyes, etc.

In all the examples the speed of the surgical thread during coating was 8 m/min.

We claim:

1. Surgical suturing thread comprising a plurality of filaments given a coating according to a process, said process comprising the steps of:
   dissolving a metal salt of a fatty acid with six or more carbon atoms in a solvent to form a solution;
   coating said plurality of filaments with said solution, the temperature of the solution being kept sufficiently high that the fatty acid metal salt remains in a dissolved state; and
   evaporating the solvent from the coating at an elevated temperature.

2. Surgical suturing thread according to claim 1, characterized in that the coating represents approximately 0.5 to 10% by weight of the coated suturing thread.

3. Surgical suturing thread according to claim 1, characterized in that the weight proportion of the wax, based on the total weight of the coating of the suturing thread is 10 to 90 and preferably 20 to 50%.

4. A surgical suturing thread according to claim 1, wherein the process further comprises the step of dissolving at least one wax in the solution prior to coating the suturing thread.

5. A surgical suturing thread according to claim 1, wherein the step of coating the suturing thread includes the passing of the suturing thread through the solution.

6. A surgical suturing thread according to claim 1, wherein said temperature is at least 50° C.

7. A surgical suturing thread according to claim 1, wherein said step of evaporating solvent occurs in a gaseous atmosphere at a gas temperature in the range of 80° C. to 200° C.

8. A surgical suturing thread according to claim 1, wherein said fatty acid metal salt comprises a single chemical compound selected from the group consisting of magnesium stearate, calcium stearate and zinc stearate.

9. A surgical suturing thread according to claim 1, wherein said fatty acid metal salt consists of a mixture of salts of several fatty acids.

10. A surgical suturing thread according to claim 1, wherein said fatty acid metal salt is selected from at least one of the group consisting of magnesium salts, barium salts, aluminum salts, zinc salts and calcium salts.

11. A surgical suturing thread according to claim 1, wherein said solvent is a terpene mixture.

12. A surgical suturing thread according to claim 1, wherein said solvent is selected from the group consisting of benzene, toluene, xylene and mesitylene.

* * * * *